(12) United States Patent
Radtke (10) Patent No.: US 9,027,391 B2
(45) Date of Patent: May 12, 2015

(54) CHROMATOGRAPHY ASSEMBLY

(75) Inventor: Jörg Radtke, Neukirchen-Vluyn (DE)

(73) Assignee: Joint Analytical Systems GmbH, Moers (DE)

( * ) Notice: Subject to any disclaimer, the term of this patent is extended or adjusted under 35 U.S.C. 154(b) by 679 days.

(21) Appl. No.: 13/044,265

(22) Filed: Mar. 9, 2011

(65) Prior Publication Data
US 2012/0060586 A1 Mar. 15, 2012

(30) Foreign Application Priority Data
Mar. 9, 2010 (DE) .......................... 10 2010 015 869

(51) Int. Cl.
*G01N 30/46* (2006.01)
*G01N 30/84* (2006.01)

(52) U.S. Cl.
CPC .............. *G01N 30/463* (2013.01); *G01N 30/84* (2013.01); *G01N 2030/8411* (2013.01)

(58) Field of Classification Search
USPC ............................................. 73/23.42, 61.56
See application file for complete search history.

(56) References Cited

U.S. PATENT DOCUMENTS

| | | | |
|---|---|---|---|
| 5,522,988 A * | 6/1996 | Cortes et al. ................ | 210/198.2 |
| 7,383,718 B2 | 6/2008 | McCurry et al. | |
| 7,518,103 B2 * | 4/2009 | Amirav ......................... | 250/281 |
| 2004/0093933 A1 | 5/2004 | Berger et al. | |
| 2004/0182134 A1* | 9/2004 | Staphanos et al. ........... | 73/23.35 |
| 2005/0218055 A1 | 10/2005 | Hayashi et al. | |
| 2007/0214866 A1* | 9/2007 | Wang ............................ | 73/23.42 |
| 2010/0101411 A1* | 4/2010 | Tipler .............................. | 95/86 |

FOREIGN PATENT DOCUMENTS

WO WO 2009/154984 A1 12/2009

OTHER PUBLICATIONS

Sweeney, Alan P., Shalliker, R. Andrew, Development of a two-dimensional liquid chromatography system with trapping and sample enrichment capabilities, Journal of Chromatography A, 2002, 41-52, 968.

* cited by examiner

*Primary Examiner* — Paul West
(74) *Attorney, Agent, or Firm* — Thorpe North & Western, LLP

(57) ABSTRACT

Chromatography assembly for multi-dimensional chromatography, includes a first separating column (12; 112) for separating a sample into components; a second separating column (13; 114) having different separating characteristics for further separating the components separated in the first separating column (12; 112); a collecting volume (20; 120, 121) for collecting the components from the first separating column (12; 112) before entering the second separating column (14; 114); a switching assembly (22, 24; 122, 124) for switching from a first state (FIG. 1; FIG. 3), where the components leaving the first separating column (12; 112) are collected in the collecting volume (20; 120, 121) to a second state (FIG. 2; FIG. 4) where the components collected in the collecting volume (20; 120, 121) are transferred to the second separating column (14; 114); and a detector (18; 118) for detecting sample components leaving the second separating column (14; 114). The volume of the collecting volume (20; 120, 121) is variable. A further collecting volume (121) may be provided and fluid flow can be through the first collecting volume (120) in the first state and through the second collecting volume (121) in the second state.

16 Claims, 7 Drawing Sheets

Fig. 3  dual volume collection step 1

Fig. 5     different collecting volumes collecting volume of 200μl is half filled after about 6 sec.

2.25mm x 50mm gas flow: 1ml/min = 15μl/s
volume velocity: 30cm³/s gas flow: 1ml/min = 15μl/s
volume velocity: 0.4cm³/s gas flow: 20ml/min = 333μl/s
volume velocity: 500cm³/s collecting volume of 62μl is half filled after about 2 sec.

1.25mm x 50mm gas flow: 1ml/min = 15μl/s
volume velocity: 30cm³/s gas flow: 1ml/min = 15μl/s
volume velocity: 1.2cm³/s gas flow: 20ml/min = 333μl/s
volume velocity: 500cm³/s Fig. 7     dual volume collection for HPLC

CHROMATOGRAPHY ASSEMBLY

TECHNICAL FIELD

The invention relates to a chromatography assembly and a method for multi-dimensional chromatography.

One such chromatography assembly for multi-dimensional chromatography comprises:
(a) a first separating column for separating a sample flowing through the separating column into components;
(b) a second separating column for further separating the components separated in the first separating column, wherein the second separating column has different separating characteristics than the first separating column;
(c) a collecting volume for collecting the components before entering the second separating column the collecting volume being arranged in the flow path between the first and the second separating column;
(d) a switching assembly for switching the chromatography assembly from a first state, where the components leaving the first separating column are collected in the collecting volume to a second state where the components collected in the collecting volume are transferred to the second separating column; and
(e) a detector for detecting sample components leaving the second separating column.

One such method for generating a multi-dimensional chromatogram comprises the steps of:
(a) Separating a sample in a first separating column in a plurality of components;
(b) Collecting the components in a collecting volume;
(c) Separating the collected components in a second separating column; and
(d) Detecting the components separated in the second separating column.

Such assemblies are known as multi-dimensional or comprehensive chromatography assemblies. In the field of gas chromatography the assemblies and the method are called "GC×GC" or "GC–GC" and in the field of high-performance liquid chromatography (HPLC) are referred to as "LC×LC". There are mixed assemblies known, such as GC×LC and LC×GC. The assemblies are characterized in that a sample flows through two different columns having different separating characteristics. Non-resolved peaks from the first separating column can be separated in the second separating column. In such a way a very high resolution is achieved.

Known assemblies are based on one of two different principles: One alternative is to freeze separated components in the first separating column by means of a freezing agent, such as nitrogen and to release them after the collection by heating. The other alternative is to switch the fluid flow through the columns and a collecting volume in such a way that the components are cyclically collected in the collecting volume and transferred to the second separating column afterwards. Thereby the use of an expensive freezing agent is avoided. The present invention relates to the latter assembly and method where states are switched by a suitable flow management.

U.S. Pat. No. 7,383,718 B2 (McCurrey) discloses an assembly with a first and a second separating column which are used to carry out two-dimensional gas chromatography. A "flow modulator" with a valve and a pressure control switches the flows in a desired way. Such an assembly is commercially sold by Agilent Technologies Corp. under the name "Agilent 7890A GC System". In a first step the components separated in the first separating column are collected in a collecting volume. In a second step the collected components are very quickly transferred to the second separating column for further separation. For this purpose, a carrier gas flow is flowed through the collecting volume during the second step. During the collection such carrier gas flow is bypassed around the collecting volume.

Depending on the flow conditions, the design of the columns, and on the application, too much of the mobile phase leaving the first column may enter the collecting volume. In other words: the collecting volume may become full. In such instance, a portion of the components will already enter the second separating column before the transfer step. This is not desirable. However, a larger collecting volume is generally not desired either, as the transfer to the second column will then last a long time.

DISCLOSURE OF THE INVENTION

Aspects of the invention provide a chromatography assembly and a method of the above mentioned kind which enable higher accuracy and reduced analysis times.

According to one aspect of the invention the volume of the collecting volume is variable. The collecting volume can be, for example, formed by an exchangeable, releasably attached pipe, tube, line, or capillary or by a channel etched into a plate. However, it is also possible that the collecting volume is provided in its own module which is adapted to be exchanged as a whole. A variable collecting volume enables an adaptation to the features of the separating columns and the application conditions. The adaptation is effected in the best case scenario by a collection of up to about 50% of the collecting volume, preferably in the range between 40 and 60%. If the first separating column is designed to have a high fluid flow, it is advantageous to use a large collecting volume. This is also the case with the application of high temperatures causing a higher diffusion where a larger collecting volume is advantageous. However, in order to reduce the transfer time of the sample into the second separating column and thereby the measuring time with small fluid flow in the first separating column, it is advantageous to select a smaller collecting volume. The adaptation of the collecting volume is carried out by selecting a line portion or capillary portion matching the selected application and the first separating column, which may then be, for example, screwed to matching connectors of the assembly. Advantageously, the collecting volume has always a larger inner diameter than the first separating column. The line or capillary portion or the exchangeable module is preferably made of metal when used in gas chromatography, whereas it is preferably made of an inert polymer for use in liquid chromatography.

The assembly is particularly suitable with gas chromatography separating columns or liquid chromatography separating columns or a combination thereof.

In a particularly preferred embodiment of the invention, the collecting volume is adapted to be heated. The second separating column preferably has the same temperature as the first separating column. Alternatively, the separating columns are separately maintained at constant temperature.

In a further modification of the invention, the switching assembly comprises a fluid source having a flow or pressure control for generating a fluid flow and a valve for flowing the fluid flow through the collecting volume in the second state.

In a particularly preferred further modification of the invention, a further collecting volume is provided and the fluid flow is flowed through the first collecting volume in the first state and through the second collecting volume in the second state. With such an assembly the collected components from one collecting volume can be transferred to the second separating column simultaneously with a collection in the other collecting volume. Thereby, no sample components are lost for detection. A further advantage of the use of two collecting volumes is the sample transfer over a longer period of time without increasing the duration of the measurement. The transfer to the second separating column can be effected with smaller volume velocities than with the use of only one collecting volume.

The generation of a multi-dimensional chromatogram according to the present invention is characterized in that the collecting volume is adapted to the characteristics of the columns and to the operation conditions. For the collection of the components the assembly is preferably switched between at least two collecting volumes and the collection is achieved in one collection volume while components collected in the other collecting volumes are transferred to the second column, and vice versa.

A liquid may be used as a carrier and the detection may be achieved by means of mass spectrometry with the method according to the present invention. It is understood, however, that the invention may also be used with gas chromatography in addition to or instead of liquid chromatography (LC×LC) or other methods and detection methods may be used, such as UV detection, diode-array detection (DAD) or flame ionization detection (FID).

For switching between the collecting volumes a controlled fluid flow is preferably used which is alternately flowing through the collecting volumes and the inlet pressure of the fluid flow is adjustable and variable in time. The fluid flow is then kept small in the collecting volume where the components are transferred to the second separating column.

Example embodiments are described below in greater detail with reference to the accompanying drawings.

DESCRIPTION OF PREFERRED EMBODIMENTS

Figure 1:
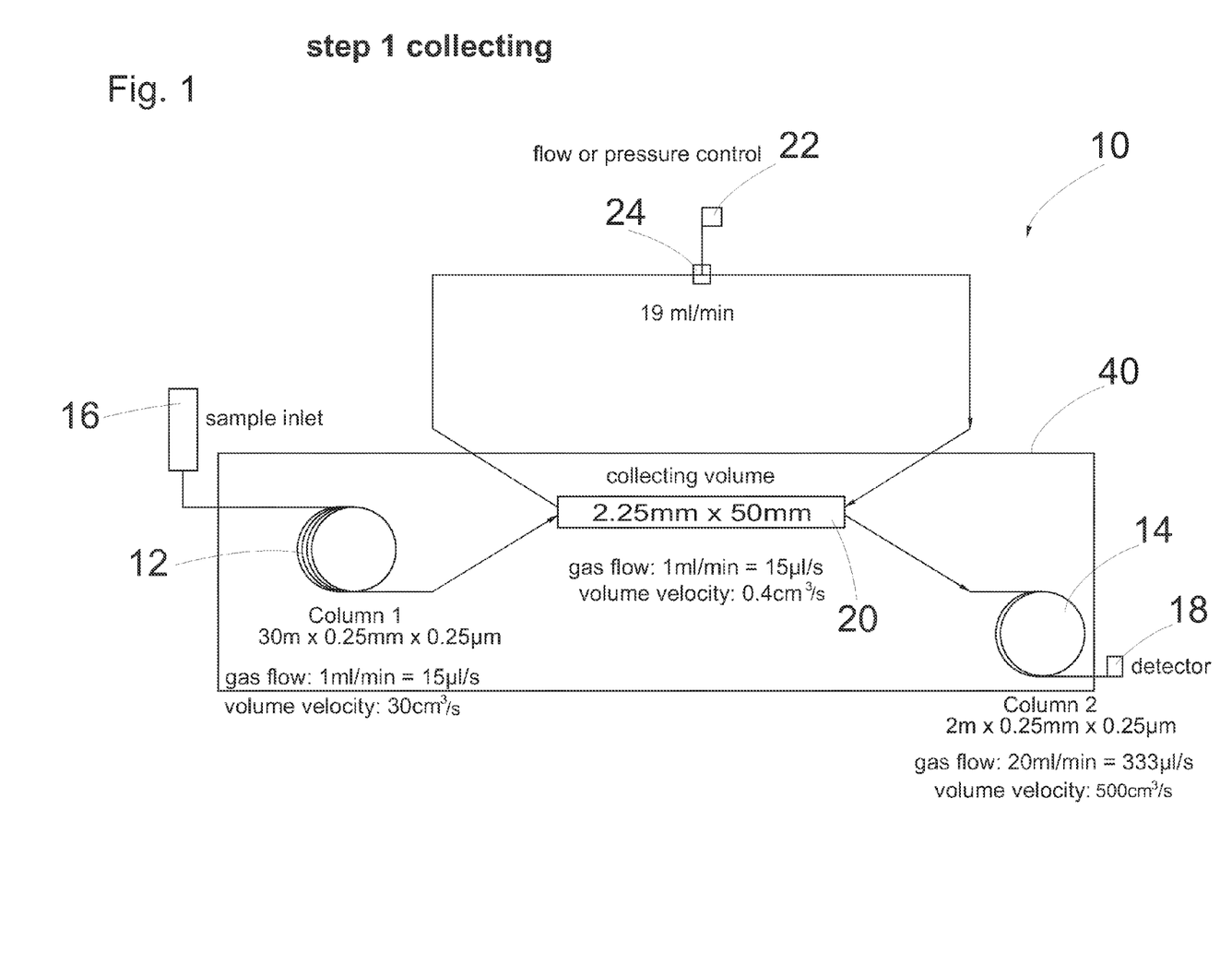
FIG. 1 is a schematic representation of a multi-dimensional chromatography assembly with a collecting volume in its collecting state.

FIG. 1 shows an assembly for multi-dimensional chromatography generally denoted with numeral 10. The assembly comprises a first separating column 12 and a second separating column 14. Depending on the application the separating columns 12 and 14 are designed for gas chromatography or liquid chromatography. The separating columns 12 and 14 are serially connected. A sample flowing from a sample inlet 16 through the first separating column 12 will flow afterwards completely through the second separating column 14 also. A detector 18 is provided at the exit of the second column 14.

Any detector is suitable as detector 18, which is suitable for the otherwise known chromatography assemblies, such as, for example, UV detection, atomic emission detection (AED), mass spectrometer detection (MS), flame ionization detection (FID), etc.

The separating column 12 has a different stationary phase than the separating column 14. In such a way, non-resolved peaks of different components entering the separating column 14 from the separating column 12 are resolved.

A collecting volume 20 is provided between the first separating column 12 and the second separating column 14. In the present embodiment, the collecting volume 20 is a capillary releaseably screwed to both ends of the separating columns 12 and 14 by means of a multipath screw assembly. The capillary forms an exchangeable module together with the screw assembly. In the field of gas chromatography the module is made of high temperature stable, inert stainless steel. In the field of liquid chromatography the module is made of an inert polymer material.

Figure 2:
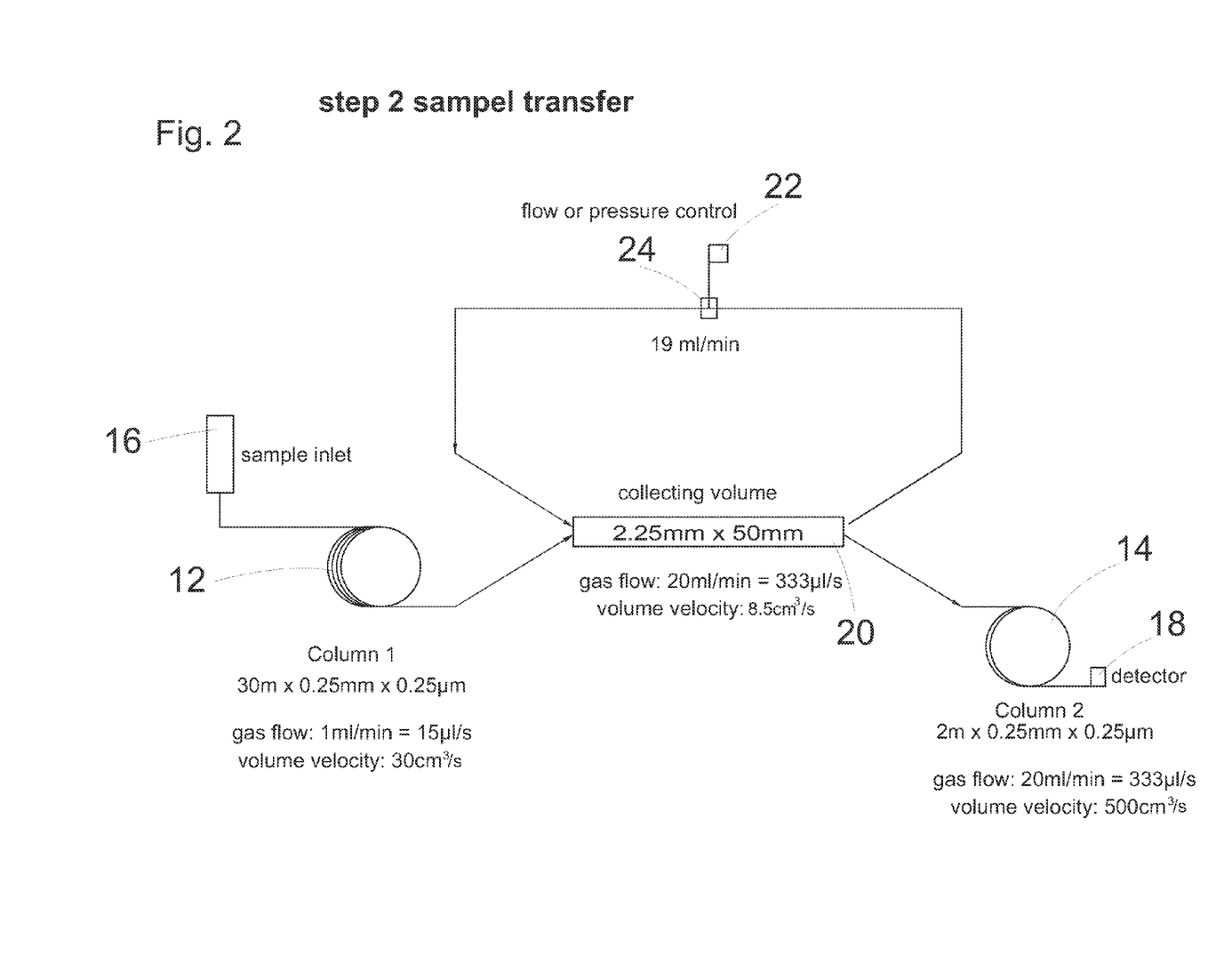
FIG. 2 shows the assembly of FIG. 1 during the transfer of the components collected in the collecting volume into the second separating column.

A carrier fluid source 22 is provided in order to influence the flow in the collecting volume 20. In gas chromatography, the carrier gas comes from the carrier gas fluid source 22, such as, for example, molecular hydrogen. On one side, the carrier gas fluid source 22 is connected to the inlet of the collecting volume 20 at the module through a valve 24. On the other side, the carrier gas source 22 is connected to the outlet of the collecting volume 20 through the valve 24 and thereby with the inlet of the second separating column 14. Depending on the position of the valve 24, the carrier fluid flow is either flowed through the collecting volume 20 or bypasses the collecting volume 20. FIG. 1 shows the assembly where the carrier fluid flow from the carrier gas fluid source 22 is bypassed around the collecting volume 20 by the valve 24 and to the second separating column 14. FIG. 2 shows the assembly where the carrier fluid flow from the carrier gas fluid source 22 flows through the valve 24 and through the collecting volume 20 to the second separating column 14.

The assembly operates as follows: A sample having several components enters the first separating column 12 through the sample inlet 16. The components of the sample are separated as well as possible. From there the components enter the collecting volume 20.

In a first step of the cycle, shown in FIG. 1, the carrier fluid, as shown in FIG. 1, bypasses the collecting volume and flows to the second separating column 14. The sample is collected in the collecting volume 20 where it is moved with small volume velocity. The volume velocity corresponds to the relatively small gas flow in the first separating column 12 causing a small volume velocity if the collecting volume 20 is essentially larger than the volume of the first separating column. This is the collecting step.

In a second step of the cycle, shown in FIG. 2, the carrier fluid flows, as shown in FIG. 2, through the collecting volume 20 to the second separating column 14. The sample collected in the collecting volume 20 is then transferred to the second separating column with a relatively high volume velocity. The volume velocity corresponds to the gas flow resulting from the sum of the gas flow from the first separating column 12 and the gas flow of the carrier fluid source.

The first and the second step of the cycle are repeated until the entire sample has flowed through the assembly. The duration of the cycle depends on the application and the measuring conditions. A flow and/or pressure control provided at the fluid source enables control over the volume velocities through the collecting volume 20. The collecting volume 20 in the form of a module is provided with a capillary having a fixed length. The inner diameter of the capillary, however, is chosen in such a way that with the given diameters of the first separating column and the selected duration of the cycle, a collection of the sample of about 50% of the collecting volume is achieved. Thereby, for each kind of sample and each kind of column a premature leaving of the sample during the collecting phase is avoided and still a short measuring time is achieved. If the assembly is operated with a different column, the module is exchanged. For this purpose the connectors connecting the fluid source and the separating columns are released and a different module is inserted.

By way of example, FIGS. 1 and 2 show values for typical gas flows and volume velocities for a gas chromatography application. The sample flows together with a carrier gas with a gas flow of 1 ml/min corresponding to 15 μl/s through the first separating column 12. The size of the separating column is about 30 m×0.25 mm×0.25 μm. The mobile phase has a volume velocity of 30 cm$^3$/s. The collecting volume has a size of 2.25 mm×50 mm. According to the larger cross section and the gas flow of 1 ml/min in the collecting phase a smaller volume velocity of 0.4 cm$^3$/s is obtained. The second, subsequent separating column 14 again has a smaller cross section with the size of 2 m×0.25 mm×0.25 μm. The gas flows from the collecting volume and from the carrier gas source 22, 19 ml/min in the present example, are added up. Accordingly, a gas flow of 20 ml/min is generated in the second separating column 14 during the collecting phase. The resulting volume velocity is 500 cm$^3$/s which is high.

Figure 5:
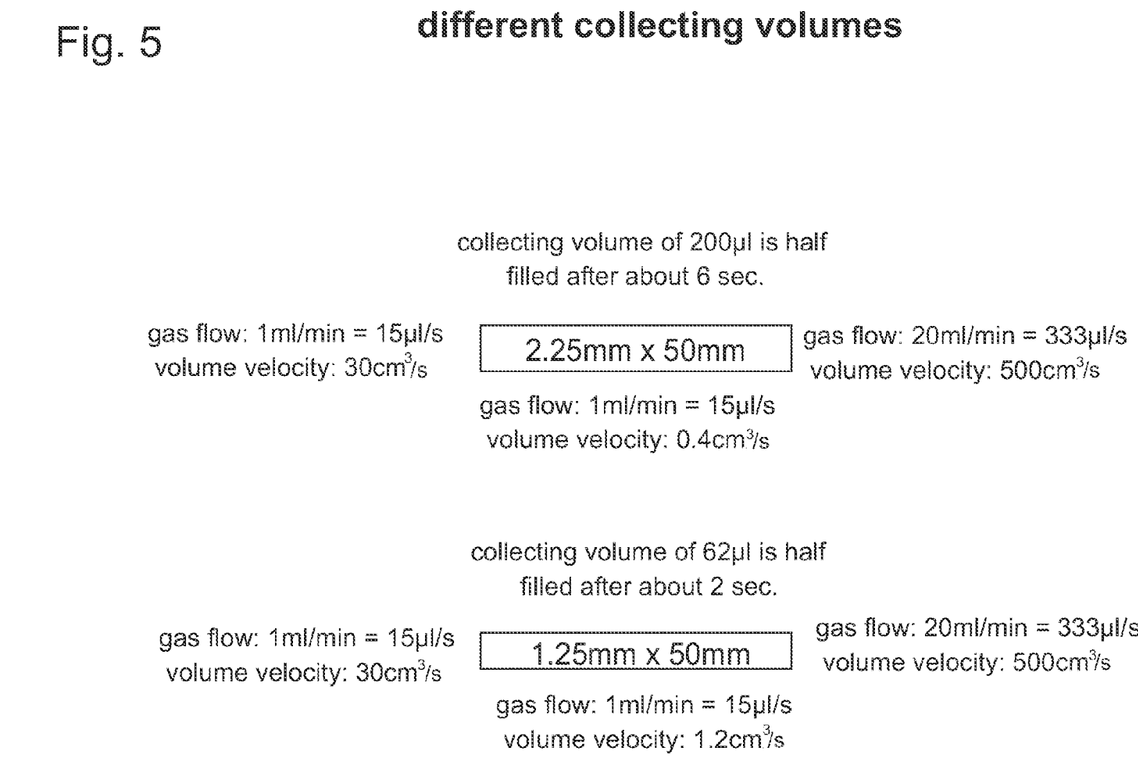
FIG. 5 illustrates the effects of a variable collecting volume for a first separating column with a gas flow of 1 ml/min.

The carrier gas flow from the carrier gas source 22 flows through the collecting volume during the transfer phase (FIG. 2). Here also the gas flows are added up to 20 ml/min. This corresponds to a higher volume velocity of 8.5 cm$^3$/s. It can be seen, that the higher volume velocity causes a quicker transfer of the collected sample to the second separating column. If the size or the gas flows in the first column are changed the time until the collecting volume 20 is "full" will change. This can be seen from the values in FIG. 5. The sizes and values given in FIG. 1 causes the collecting volume of 200 μl to be half filled in about 6 seconds. A smaller collecting volume of 62 μl with the diameters of 1.25 mm×50 mm will need a filling time of only about 2 seconds. Depending on the application, i.e., peak widths, sample properties, resolution of the columns, etc., a smaller or a larger collecting volume can be more favorable.

The separating columns 12 and 14 and the collecting volume 20 are arranged in an oven 40 which can be controlled up to a temperature of 30° C. In an alternative embodiment, which is not shown, the second separating column 14 is arranged in a separate oven.

Figure 3:
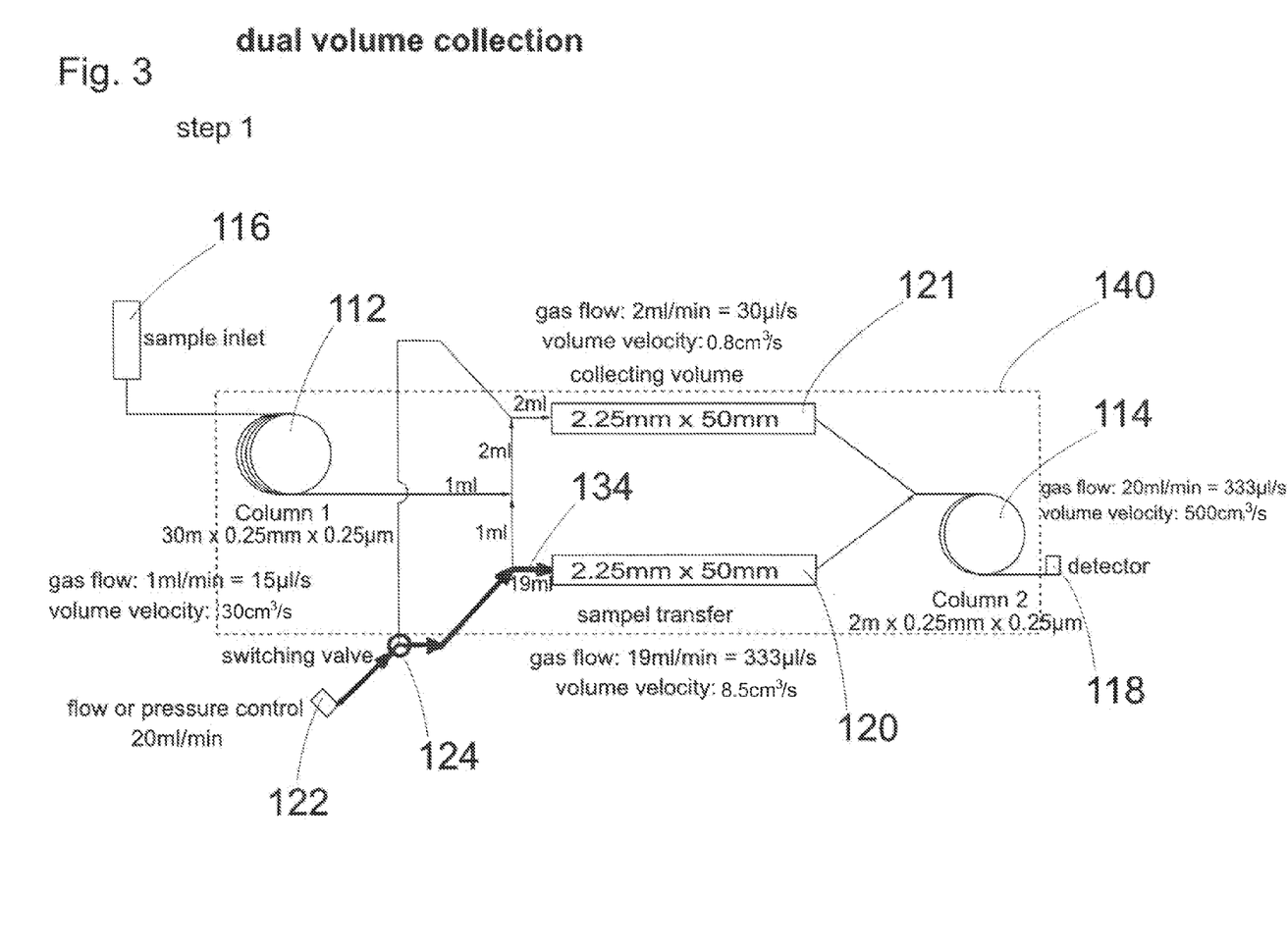
FIG. 3 is a schematic representation of a multi-dimensional chromatography assembly with two collecting volumes in a first switching state.
Figure 4:
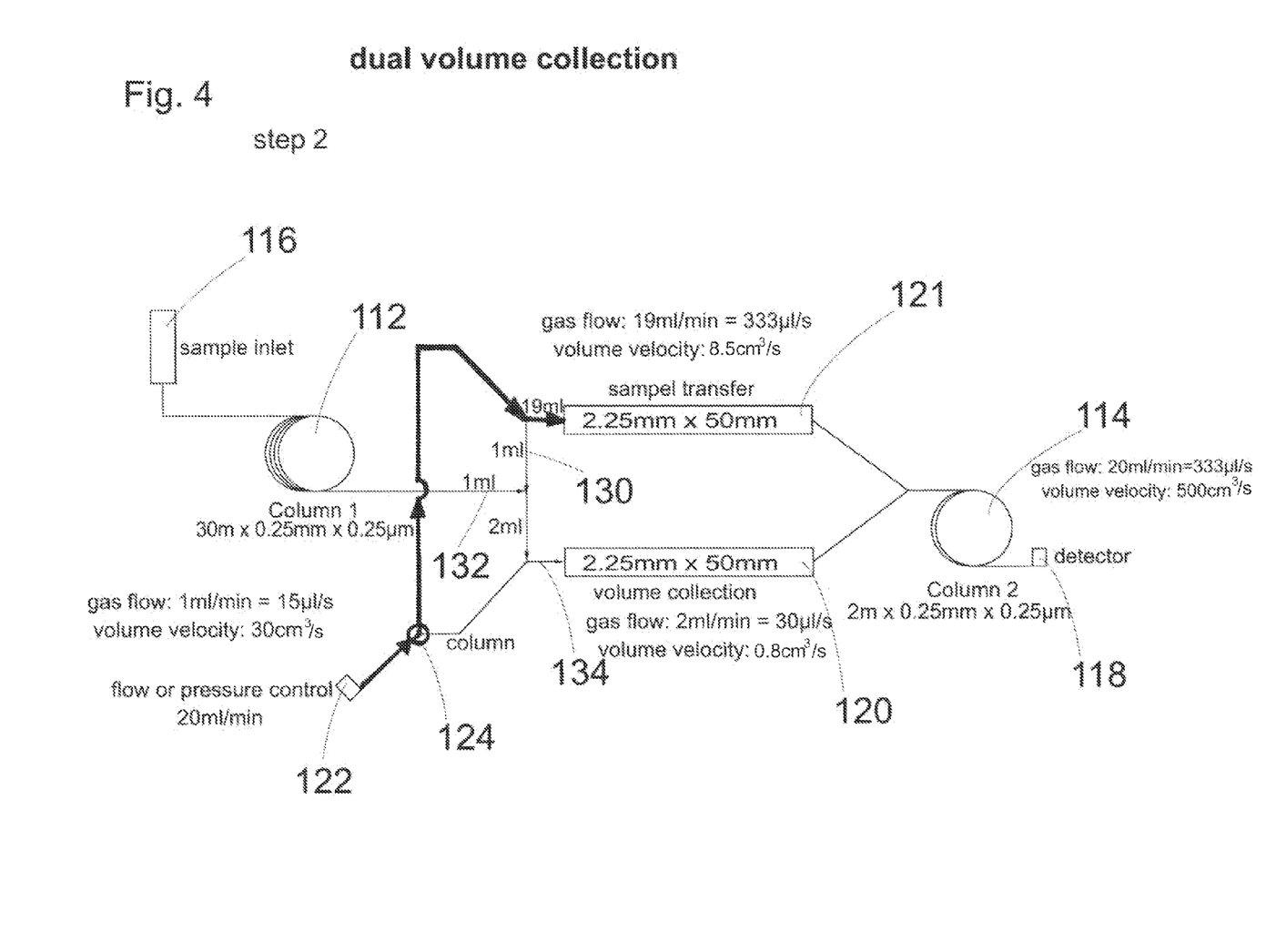
FIG. 4 shows the assembly of FIG. 3 in a second switching state.

FIG. 3 and FIG. 4 show an alternative embodiment. As in the embodiment described above, a sample inlet 116, a first separating column 112, a second separating column 114, and a detector 118 are provided. Two collecting volumes 120 and 121 are provided between the separating columns 112 and 114 in the present embodiment. The collecting volumes 120 and 121 are capillaries which are positioned in a common releasable module. Each of the collecting volumes is connected to the outlet of the first separating column 112 with an inlet. Furthermore, a connector to a fluid source 122 with a flow and/or pressure control is connected to the inlets of the collecting volumes. The fluid flow from the fluid source 122 can be conveyed to the inlets by a switching valve 124. The outlets of the collecting volumes 120 and 121 are connected to the second separating column 114.

The assembly operates as follows: In a first step the fluid flow 134 flows to the inlet of the collecting volume 120. Simultaneously, the separated sample from the first separating column 112 flows to the inlet of the other collecting volume 121. The sample is collected in the collecting volume 121 during this step. The content of the collecting volume 120 is transferred to the second separating column with the fluid flow. This situation is shown in FIG. 3. By switching the switching valve 124 the fluid flow is directed to the inlet of the collecting volume 121. The sample leaving the first separating column 112 flows to the inlet of the collecting volume 120. There, the sample is collected. This state is shown in FIG. 4. It can be well recognized that in such an assembly the sample will always be collected in either one of the two collecting volumes while the content of the respective other one of the collecting volumes is transferred to the second separating column. In such a way a continuous collection is achieved and the process is not interrupted by transferring the sample to the second separating column. Accordingly, the transfer may take more time.

In order to have the sample leaving the first separating column entering the desired collecting volume a small flow portion 130 of the fluid flow is separated before the inlet of the collecting volume and flows to the other inlet together with the sample flow 132. In FIG. 4, for example, a flow portion 130 of the fluid flow is separated and flows to the inlet 134 of the collecting volume 120. In FIG. 3 the situation is exactly the opposite. The cross section of the line for the fluid portion 130 is essentially smaller than the cross section of the line for the remaining fluid flow resulting in a corresponding separation without any further control means. This line forms a restriction to provide for a complete transfer of the collecting volume 120 or 121, respectively, with the components from the first separating column 112. The separating columns 112 and 114 and the collecting volumes 120 and 121 are arranged in an oven with a controlled temperature of up to 300° C. In an alternative embodiment which is not shown the second separating column 114 is arranged in a separate oven.

By way of example some typical values of the flow conditions shall be illustrated below. It is understood, however, that this serves for illustration of the way of operation only and that the invention is by no means limited to such values.

The carrier gas source is controlled to a gas flow of 20 ml/min as described in the above embodiment and the gas flow in the first separating column is 1 ml/min. In the step shown in FIG. 3 the sample flows into the collecting volume 121. Accordingly, 19 ml/min of a total of 20 ml/min of the carrier gas will flow through the collecting volume 120. 1 ml/min of the carrier gas flows through the collecting volume 121 together with the sample. The gas flow therein is 2 ml/min corresponding to a slow volume velocity of 0.8 cm$^3$/s. The volume velocity inside the collecting volume 120 where the content is transferred to the second separating volume is 8.5 cm$^3$/s. The flow conditions in the situation shown in FIG. 4 are exactly the opposite.

Figure 6:
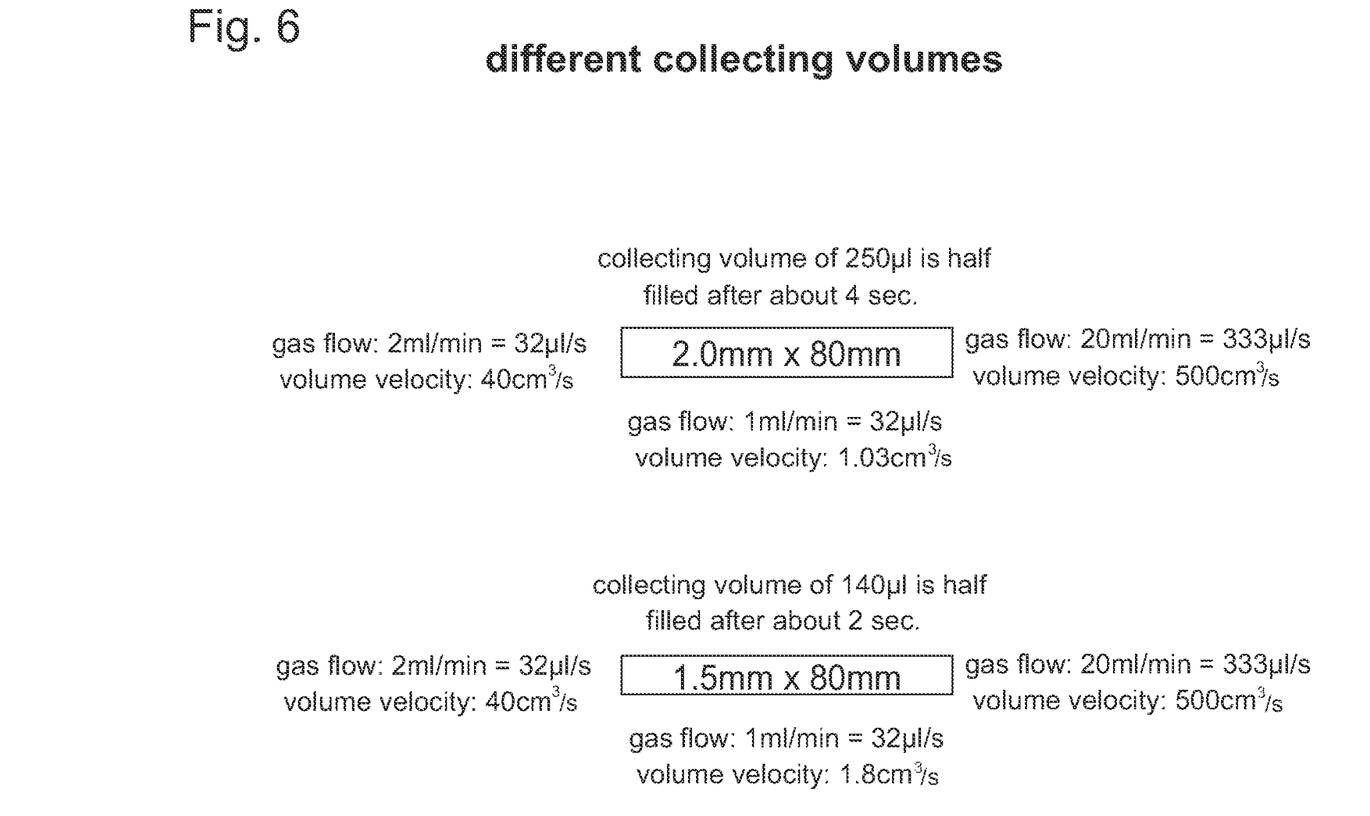
FIG. 6 illustrates the effects of a variable collecting volume for a first separating column with a gas flow of 2 ml/min.

The effects of changing the collecting volume are shown in FIG. 6 by way of example: The reduction of the collecting volume causes a higher volume velocity and, thereby, a quicker filling.

If the transfer to the second separating column 114 shall be effected more slowly, the carrier gas flow is reduced by the corresponding collecting volume. This can be done by a flow or pressure control varying in time or by a bypass.

Figure 7:
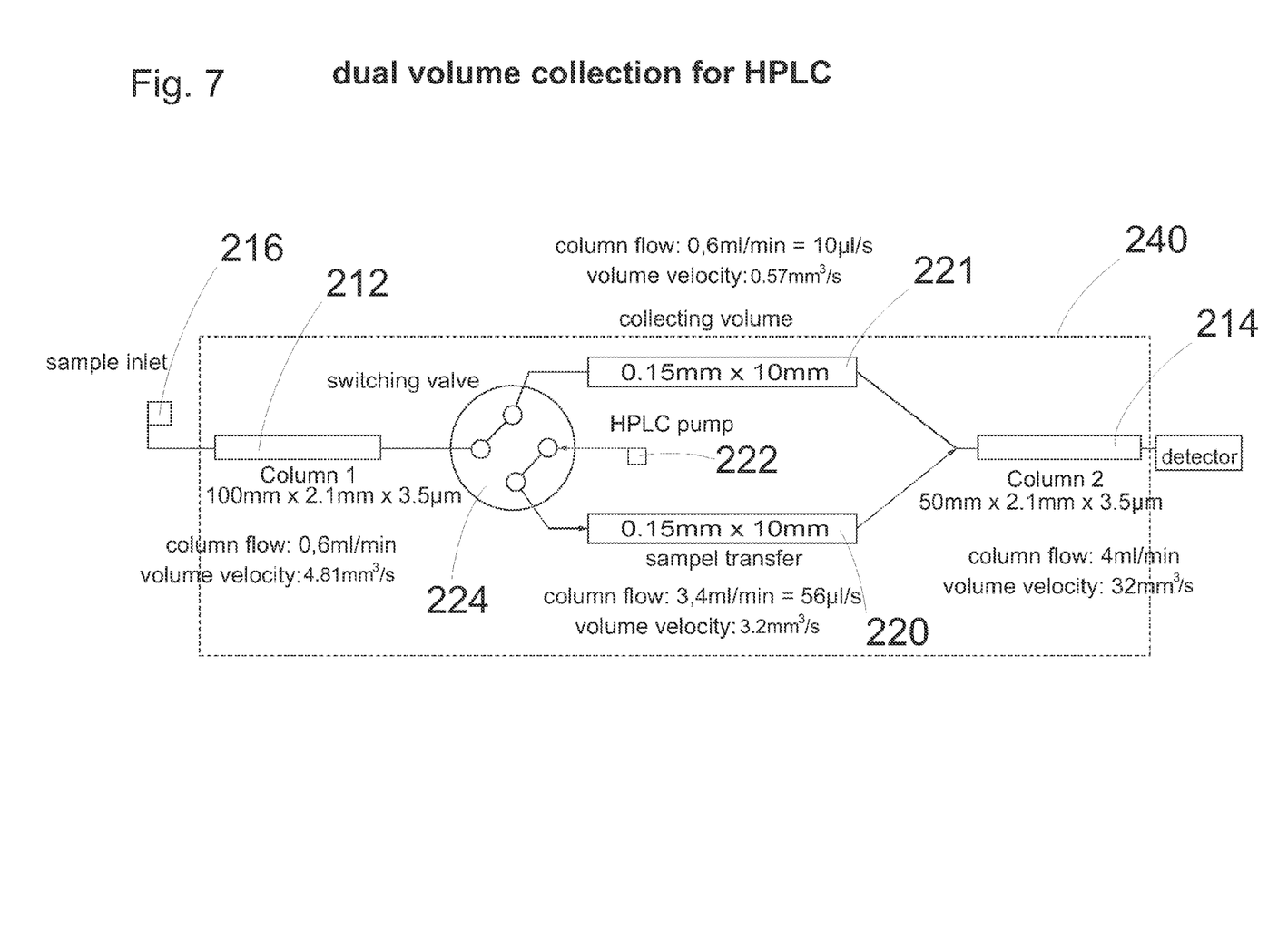
FIG. 7 shows an assembly for LC×LC with two collecting volumes and an alternative switching valve.

FIG. 7 shows a HPLC assembly where different volume velocities are present than in the above examples for gas chromatography. The inlets of the collecting volumes 220 and 221 receive the sample from the sample inlet 216 through a common switching valve 224. The switching valve 224 directs the mobile phase to either one of the collecting volumes-here denoted with numeral 221. Only mobile phase from the HPLC-pump 222 flows through the other collecting volume 220 similar to the example of FIGS. 3 and 4. The switching valve 224 enables a particularly simple handling in the HPLC because operation is isothermal—contrary to the gas chromatography. An oven 240 is provided for this purpose in order to maintain the separating columns 212 and 214 and the collecting volumes 221 and 220 constantly in the range of 30° C.

The flow flows from the first separating column 212 with a volume velocity of about 4.81 mm$^3$/s through the switching valve 224 to the collecting volume 221. The volume velocity is there reduced to 0.57 mm$^3$/s due to the larger cross section. The sample in the collecting volume 220 is transferred to the separating column 214 with a volume velocity of 3.2 mm$^3$/s. Such an assembly is particularly suitable for MS-detectors.

Whereas the invention is here illustrated and described with reference to example embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. Chromatography assembly for carrying out a multi-dimensional chromatography analysis of a sample, comprising
   (a) a first separating column for separating said sample flowing through said separating column into components;
   (b) a second separating column for further separating said components separated in said first separating column, wherein said second separating column has different separating characteristics than said first separating column;
   (c) a collecting volume for collecting said components separated in said first separating column before entering said second separating column said collecting volume being arranged in a flow path between said first and said second separating column, said flow path between said first separating column and said second separating column having a collecting volume receiving space therein for removably and interchangeably receiving the collecting volume in said collecting volume receiving space, said collecting volume having a desired interior size;
   (d) a switching assembly for switching said chromatography assembly from a first state, where said components leaving said first separating column are collected in said collecting volume to a second state where said components collected in said collecting volume are transferred to said second separating column; and
   (e) a detector for detecting sample components leaving said second separating column:
   and wherein
   (f) the interior size of said collecting volume is variable by selecting the collecting volume of the desired interior size to be received in the collecting volume receiving space for a particular multi-dimensional chromatography analysis.

2. Chromatography assembly according to claim 1, wherein said collecting volume is formed by an exchangeable, releasably attached pipe, tube, line or capillary or by a channel etched into a plate.

3. Chromatography assembly according to claim 1, wherein said separating columns are gas chromatography separating columns or liquid chromatography separating columns or a combination thereof.

4. Chromatography assembly according to claim 1, wherein said collecting volume is adapted to be heated.

5. Chromatography assembly according to claim 1, wherein said switching assembly comprises a fluid source having a flow- or pressure control for generating a fluid flow and a valve flowing said fluid flow through said collecting volume in said second state.

6. Chromatography assembly according to claim 1, wherein a further collecting volume is provided and said fluid flow is flowed through said first collecting volume in said first state and through said second collecting volume in said second state.

7. Chromatography assembly according to claim 1, wherein the collecting volume is formed by a capillary column.

8. Chromatography assembly according to claim 1, additionally including a plurality of collecting volumes, each collecting volume of the plurality of collecting volumes adapted to be removably and interchangeably inserted into the collecting volume receiving space and each collecting volume having a different interior size whereby the interior size of the collecting volume is variable by which of the collecting volumes of the plurality of collection volumes is inserted into the collecting volume receiving space.

9. Method for generating a multi-dimensional chromatogram of a sample material comprising the steps of:
   obtaining a chromatography assembly having a first separating column having first column characteristics, a second separating column having second column characteristics, and a flow path between said first separating column and said second separating column having a collecting volume receiving space therein for removably and interchangeably receiving a collecting volume in said collecting volume receiving space;
   selecting operating conditions for the chromatography assembly for generating the multi-dimensional chromatogram of the sample material;
   determining from one or more of the first and second column characteristics and from the selected operating conditions a desired volume of sample to be collected from the first column to then be fed to the second column;
   obtaining a collecting volume having an interior size to hold a sample volume approximating the desired volume of sample to be collected;
   removably and interchangably connecting the obtained sample volume in the collecting volume receiving space in the flow path between the first separating column and the second separating column;
   separating the sample in the first separating column into a plurality of components;
   collecting said components in the collecting volume;
   separating said collected components in the second separating column; and
   detecting said components separated in said second separating column;
   and wherein
   said collecting volume is adapted to one or more of the characteristics of said columns and operating conditions.

10. Method according to claim 9, wherein for said collection of said components an assembly of any of claims 1 to 7 is used which is switched between at least two collecting volumes and said collection is achieved in a collection volume while components collected in said other collecting volume are transferred to said second column and vice versa.

11. Method according to claim 10, wherein a controlled fluid flow is used for switching between said collecting volumes which is alternately flowed through said collecting volumes and an inlet pressure of said fluid flow is adjustable and variable in time.

12. Method according to claim 9, wherein a liquid is used as a carrier and said detection is achieved by means of mass spectrometry.

13. Chromatography assembly for carrying out a multidimensional chromatography analysis of a sample, comprising
  (a) a first separating column for separating said sample flowing through said separating column into components;
  (b) a second separating column for further separating said components separated in said first separating column, wherein said second separating column has different separating characteristics than said first separating column;
  (c) a collecting volume module for collecting said components separated in said first separating column before entering said second separating column said collecting volume module being arranged in a flow path between said first and said second separating column, said flow path between said first separating column and said second separating column having a collecting volume module receiving space therein for removably and interchangeably receiving the collecting volume module in said collecting volume module receiving space, said selected collecting volume module having a desired interior size;
  (d) a switching assembly for switching said chromatography assembly from a first state, where said components leaving said first separating column are collected in said collecting volume to a second state where said components collected in said collecting volume are transferred to said second separating column; and
  (e) a detector for detecting sample components leaving said second separating column:
  and wherein
  (f) the interior size of said collecting volume is variable by selecting the collecting volume module of the desired interior size to be received in the collecting volume module receiving space for a particular multi-dimensional chromatography analysis.

14. Chromatography assembly according to claim 13, wherein said collecting volume module includes a pipe, tube, line or capillary, or channel etched into a plate forming the interior size of the collecting volume.

15. Chromatography assembly according to claim 13, additionally including a plurality of collecting volume modules, each collecting volume module of the plurality of collecting volume modules adapted to be removably and interchangeably inserted into the collecting volume module receiving space and each collecting volume module having a different interior size whereby the interior size of the collecting volume is variable by which of the collecting volume modules of the plurality of collection volume modules is inserted into the collecting volume module receiving space.

16. Chromatography assembly for carrying out a multidimensional chromatography analysis of a sample, comprising
  (a) a first separating column for separating said sample flowing through said separating column into components;
  (b) a second separating column for further separating said components separated in said first separating column, wherein said second separating column has different separating characteristics than said first separating column;
  (c) a collecting volume for collecting said components separated in said first separating column before entering said second separating column said collecting volume being arranged in a flow path between said first and said second separating column;
  (d) a switching assembly for switching said chromatography assembly from a first state, where said components leaving said first separating column are collected in said collecting volume to a second state where said components collected in said collecting volume are transferred to said second separating column; and
  (e) a detector for detecting sample components leaving said second separating column:
  and
  (f) including one or more additional collecting volumes each having a different interior size and interchangeable to become the collecting volume of section (c) wherein the interior size of said collecting volume of section (c) is variable by selecting the desired collecting volume for the collecting volume of section (c).

* * * * *